United States Patent [19]

Sekii et al.

[11] Patent Number: 4,979,514

[45] Date of Patent: Dec. 25, 1990

[54] CARDIAC OUTPUT MEASUREMENT METHOD AND SYSTEM FOR THE APPLICATION OF SAME

[75] Inventors: Shigekazu Sekii; Kohji Tsuchida; Yoshio Ishitsu, all of Fuji, Japan

[73] Assignee: Terumo Kabushiki Kaisha, Tokyo, Japan

[21] Appl. No.: 432,053

[22] Filed: Nov. 6, 1989

[30] Foreign Application Priority Data

Nov. 9, 1988 [JP] Japan .................... 63-281371

[51] Int. Cl.$^5$ ........................... A61B 5/02
[52] U.S. Cl. ........................ 128/713; 128/692
[58] Field of Search .................. 128/713, 692

[56] References Cited

U.S. PATENT DOCUMENTS

| | | | |
|---|---|---|---|
| | 11/1966 | Kuether et al. | 128/692 |
| 3,595,079 | 7/1971 | Grahn | 73/204 |
| 3,678,922 | 7/1972 | Philips et al. | 128/692 |
| 3,789,831 | 2/1974 | Kopaniky et al. | 428/692 |
| 3,820,530 | 6/1974 | Gilford et al. | 128/713 |
| 3,995,623 | 12/1976 | Blake et al. | 128/419 P |
| 4,004,576 | 1/1977 | Gahwiler | 73/204 |
| 4,035,622 | 7/1977 | Obermajer | 128/713 |
| 4,230,126 | 10/1980 | Elings | 128/692 |
| 4,240,441 | 12/1980 | Khalil | 128/692 |
| 4,380,237 | 4/1983 | Newbower | 128/693 |
| 4,502,488 | 3/1985 | Degironimo et al. | 128/692 |
| 4,542,748 | 9/1985 | Rob Roy | 128/713 |
| 4,572,206 | 2/1986 | Geddes et al. | 128/692 |
| 4,595,015 | 6/1986 | Jansen et al. | 128/713 |
| 4,621,646 | 11/1986 | Bryant | 128/692 |
| 4,632,125 | 12/1986 | Webler et al. | 128/692 |
| 4,685,470 | 8/1987 | Sekii et al. | 128/692 |
| 4,841,981 | 6/1989 | Tanabe et al. | 128/692 |

FOREIGN PATENT DOCUMENTS

| | | |
|---|---|---|
| 0092438 | 4/1983 | European Pat. Off. . |
| 0070674 | 4/1984 | European Pat. Off. . |
| 0182363 | 2/1987 | European Pat. Off. . |
| 43-27683 | 11/1943 | Japan . |
| 51-185 | 5/1975 | Japan . |
| 51-10690 | 1/1976 | Japan . |
| 54-55144 | 5/1979 | Japan . |
| 57-182656 | 11/1982 | Japan . |
| 57-51413 | 12/1982 | Japan . |
| 61-125329 | 6/1986 | Japan . |
| WO88/06424 | 9/1988 | PCT Int'l Appl. . |
| 84/03431 | 9/1984 | World Int. Prop. O. . |

OTHER PUBLICATIONS

Medical and Biological Engineering, vol. 11, No. 2, Mar. '73, pp. 201–205; Stevanage/Herts (GB) A. L. Delanois: "Thermal Method for Continuous Blood Velocity Measurements in Large Blood Vessels, and Cardiac Output Determination".

Proceedings, The Ninth Annual Symposium on "Computer Applications in Medical Care", Nov. 10–Nov. 13, 1985, Baltimore, Md., edited by Michael J. Ackerman, Ph.D. (IEEE Computer Society, Computer Society Press).

"Thermal Method for Continuous Blood-Velocity . . . ", Medical & Biological Engineering, Mar. 1973, pp. 201–204.

Primary Examiner—Lee S. Cohen
Assistant Examiner—Scott M. Getzow
Attorney, Agent, or Firm—Frishauf, Holtz, Goodman & Woodward

[57] ABSTRACT

Disclosed are a cardiac output measurement method and a system for the application of the same, which perform the calibration of cardiac output by employing a blood flow velocity measurement method and perform continuous measurement of cardiac output. The system includes a blood temperature sensing element for sensing blood temperature, a blood temperature measurement circuit for generating a blood temperature signal indicative of the sensed blood temperature, an equilibrium temperature obtaining element capable of sensing cooling temperature of blood flow being heated, and an equilibrium temperature measurement circuit for generating an equilibrium temperature signal indicative of the sensed cooling temperature of blood flow heated. A corrected equilibrium temperature calculating circuit receives the signals generated by the blood temperature sensing element and the equilibrium temperature obtaining element, performs calculation for correction, and generates a corrected equilibrium temperature signal indicative of the result of the calculation. Cardiac output is calculated on the basis of the corrected equilibrium temperature signal.

7 Claims, 6 Drawing Sheets

THERMODILUTION CURVE

CARDIAC OUTPUT MEASUREMENT METHOD AND SYSTEM FOR THE APPLICATION OF SAME

BACKGROUND OF THE INVENTION

1. Field of the Invention:

The present invention relates to a cardiac output measurement method and a system for the application of the same, which are used to, for instance, examine the cardiac function or to control cardiac output during or after a heart operation.

2. Description of the Prior Art:

When cardiac output is to be measured for the purpose of, e.g., examining the cardiac function, by a right heart catheterization, the conventional practice is to employ an indicator dilution method. There are various forms of the indicator dilution method, and they include thermodilution in which the cardiac output is obtained from thermal diffusion, and dye dilution in which the cardiac output is obtained from changes in illuminance due to dye diffusion. Among these, the thermodilution, which is relatively closely related to the present invention, will be described.

When a right heart catheterization is performed utilizing thermo dilution, a catheterization is introduced in such a manner that its distal end is positioned in the pulmonary artery while its injectate injection port is positioned in a right atrium.

FIG. 4 illustrates the manner in which a catheter is introduced according to the prior art. Specifically, a catheter K is introduced from, e.g., a jugular vein, femoral vein or basilic vein. It is then passed through the superior or inferior vena cava, then through the right atrium RA and the right ventricle RV, and is held in place with its distal end positioned in the pulmonary artery. The catheter K has an indicator charge port positioned in the right atrium RA, and a thermistor T positioned in the pulmonary artery.

When an indicator (i.e., an injectate) the temperature whereof is higher or lower than the blood temperature is introduced from the charge port of the catheter K toward the right atrium RA, as the injectate diffuse through the right atrium RA and the right ventricle RV, the temperature of the injectate is diluted. The diluted temperature of the injectate is sensed by the thermister T positioned in the pulmonary artery. The sensed temperature is calculated to obtain a curve expressing the diluted temperature, i.e., a curve expressing changes in the blood temperature with the passage of time, such as that shown in FIG. 5. The area (hatched in FIG. 5) defined by the obtained curve is used in the following equation (1) developed by Stewart Hamilton, from which the cardiac output is calculated.

$$C.O. = \frac{Si \cdot Ci \cdot (Tb - Ti) Vi}{Sb \cdot Cb \cdot \int \infty \Delta \, Tbdt} \quad (1)$$

where C. O.: cardiac output, Si: specific gravity of injectate liquid, Ci: specific heat of injectate, Vi: amount of injectate, Ti: temperature of injectate, Tb: temperature of blood, Sb: specific gravity of blood, Cb: specific heat of blood, and $\int \infty \Delta Tbdt$: area of thermodilution curve.

Described above is an example a cardiac output measurement which has conventionally been performed by utilizing the thermodilution. The present applicant has already filed in Japan an application for patent through a cardiac output measurement system capable of performing cardiac output measurement continuously (the application was laid open as Japanese Patent Laid-Open No. 125329/1986).

SUMMARY OF THE INVENTION

Accordingly, an object of the present invention is to provide a cardiac output measurement method and a system for the application of the same, which are capable of performing cardiac output measurement continuously with reduced suffering upon the patient and with reduced risk of infection, while being capable, even when a probe possessing a different characteristic is used, of assuring a satisfactory level of measurement precision without requiring any extra effort by the operator.

According to the present invention, the foregoing object is accomplished by providing a cardiac output measurement method which performs the calibration of cardiac output by employing a blood flow velocity measurement method and performs continuous measurement of cardiac output. The method comprises the steps of: sensing blood temperature; generating a blood temperature signal indicative of the sensed blood temperature; sensing cooling temperature of blood flow being heated by the supply of constant electric current; generating an equilibrium temperature signal indicative of the sensed cooling temperature of blood flow heated; performing calculation upon the reception of the blood temperature signal and the equilibrium temperature signal in such a manner as to correct the value indicated by the equilibrium temperature signal by a suitable value corresponding to the value indicated by the blood temperature signal, the calculation being followed by the generation of a corrected equilibrium temperature signal indicative of the result of the calculation; and calculating cardiac output on the basis of the value indicated by the corrected equilibrium temperature signal.

Preferably, the cardiac output measurement method may further comprise the steps of: sensing, by means of a passive element, one temperature selected from the group consisting of blood temperature and cooling temperature of blood flow being heated by the supply of constant electric current, the sensing being followed by the generation of a characteristic value signal indicative of a characteristic value of the passive element; and performing calculation for correcting the value indicated by the equilibrium temperature signal on the basis of the characteristic value indicated by the characteristic value signal, the calculation being followed by the generation of a corrected equilibrium temperature signal.

In order to accomplish the above-stated object, the present invention also provides a cardiac output measurement system which performs the calibration of cardiac output by employing a blood flow velocity measurement method and performs continuous measurement of cardiac output. The system comprises: blood temperature sensing means for sensing blood temperature; blood temperature measurement circuit means connected to the blood temperature sensing means so as to generate a blood temperature signal indicative of the sensed blood temperature; equilibrium temperature obtaining means capable of sensing cooling temperature of blood flow being heated by heating means supplied with constant electric current; equilibrium temperature measurement circuit means connected to the equilibrium temperature obtaining means so as to generate an equilibrium temperature signal indicative of the sensed cooling temperature of blood flow heated; corrected equilibrium temperature calculating means for receiving the blood temperature signal and the equilibrium temperature signal, for performing calculation whereby the value indicated by the equilibrium temperature signal is corrected by a suitable value corresponding to the value indicated by the blood temperature signal, and for generating a corrected equilibrium temperature signal indicative of the result of the calculation; and cardiac output calculating means for calculating cardiac output on the basis of the value indicated by the corrected equilibrium temperature signal.

Preferably, the cardiac output measurement system according to the present invention may further comprise: characteristic value measurement circuit means having a passive element provided in one means selected from the group consisting of the blood temperature sensing means and the equilibrium temperature obtaining means, the characteristic value measurement means being connected to one means selected from the group consisting of the blood temperature sensing means and the equilibrium temperature obtaining means so as to generate a characteristic value signal indicative of a characteristic value of the passive element; and corrected equilibrium temperature calculating circuit means for performing calculation for correcting the value indicated by the equilibrium temperature signal on the basis of the characteristic value indicated by the characteristic value signal, and for generating a corrected equilibrium temperature signal.

The passive element may preferably be a resistor.

In the system according to the present invention having the above-described arrangement, the following operation is provided. When cardiac output measurement is not performed by utilizing thermodilution, a cardiac output value input means incorporated in the system allows a certain cardiac output value set by the measurer to be transmitted, as the cardiac output calibration value, to the cardiac output calculating means. Subsequently, the blood temperature sensing means senses, by its temperature sensing element, the body temperature prevailing in its central portion, i.e., the blood temperature, and the sensing means generates an electrical signal indicative of the sensed blood temperature.

The blood temperature-indicative electrical signal is sent to the blood temperature measurement circuit means connected to the blood temperature sensing means. The blood temperature measurement circuit means amplifies and biases the blood temperature-indicative electrical signal so that the value indicated by the electrical signal can be properly related with temperature.

The equilibrium temperature obtaining means has its self-heating type sensing element heated by constant electric current, and the sensing means obtains the equilibrium temperature achieved as a result of the sensing element being cooled by blood flow. The obtained equilibrium temperature is generated as an electrical signal indicative of the obtained equilibrium temperature.

The equilibrium temperature-indicative electrical signal is sent to the equilibrium temperature measurement circuit means connected to the equilibrium temperature obtaining means. The equilibrium temperature measurement circuit means amplifies and biases the equilibrium temperature-indicative electrical signal so that the value indicated by the electrical signal can be properly related with temperature.

The passive element is provided in either of the blood temperature sensing means and the equilibrium temperature obtaining means so as to obtain a value corresponding to the characteristic of the probe used. The blood temperature sensing means or the equilibrium temperature obtaining means is connected to the characteristic value measurement circuit means. The characteristic value measurement circuit means measures a characteristic value of the passive element, generates a characteristic value signal indicative of the measured characteristic value of the passive element, and sends this signal to the corrected equilibrium temperature calculating circuit means.

The corrected equilibrium temperature calculating circuit means receives the blood temperature-indicative electrical signal, the equilibrium temperature-indicative electrical signal and the characteristic value signal from the blood temperature measurement circuit means, the equilibrium temperature measurement circuit means and the characteristic value measurement circuit means, respectively. Upon receiving these signals, the circuit performs calculation for correction of the value of the equilibrium temperature-indicative electrical signal in accordance with the values of the blood temperature signal and the characteristic value signal, and generates a corrected equilibrium temperature signal indicative of the result of this calculation.

The corrected equilibrium temperature signal is sent to the blood flow velocity calculating means which in turn calculates blood flow velocity, and generates a signal indicative of the calculated blood flow velocity. This signal is sent to the cardiac output calculating means in which the signal is then used in the calculation of cardiac output. The calculated cardiac output is finally output and displayed by a display incorporated in the system.

DESCRIPTION OF THE PREFERRED EMBODIMENT

The present invention will now be described with reference to the drawings.

Figure 1A:
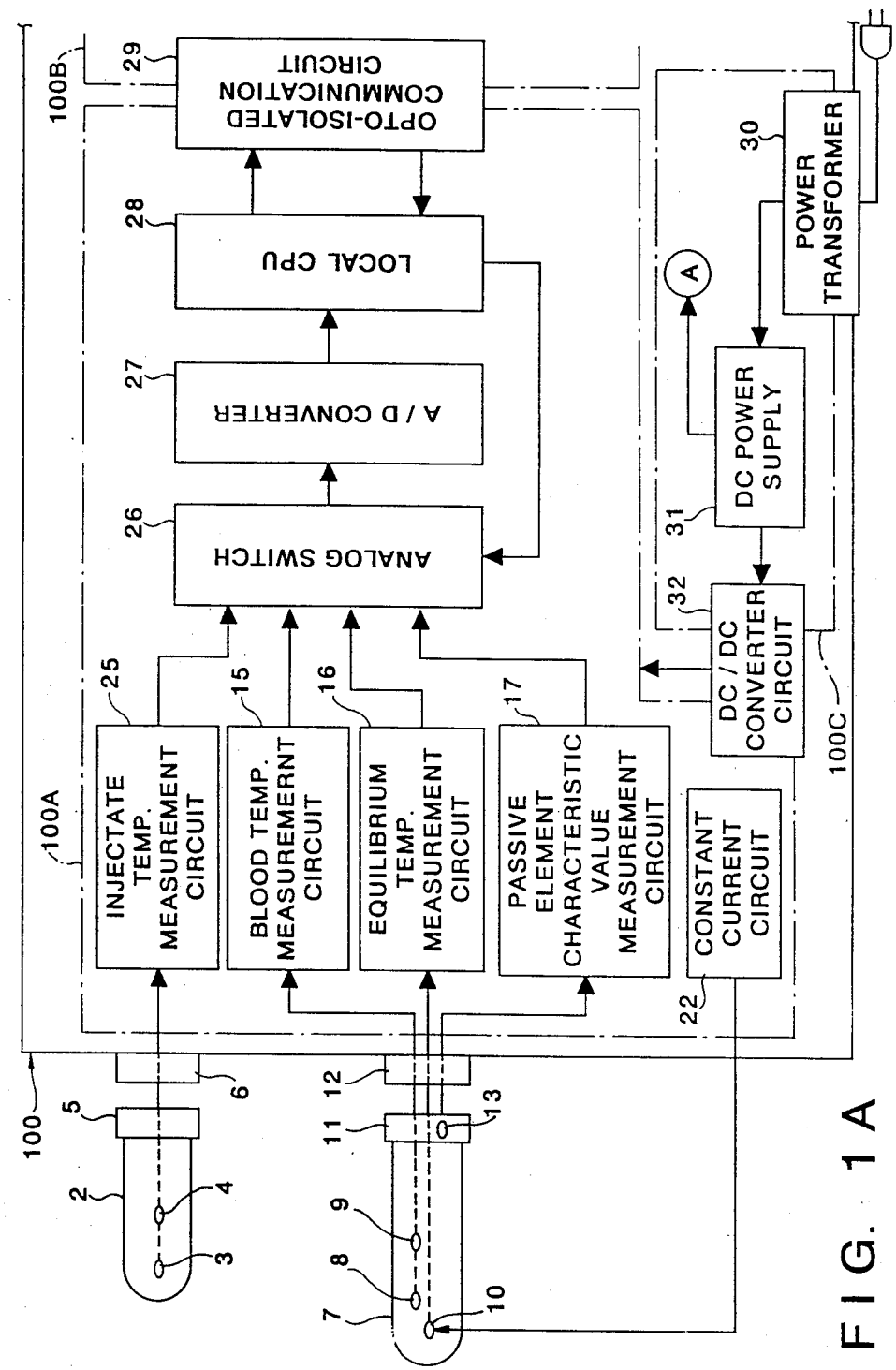
FIG. 1A and 1B are block diagrams illustrating a cardiac output measurement system according to the present invention.
Figure 1B:
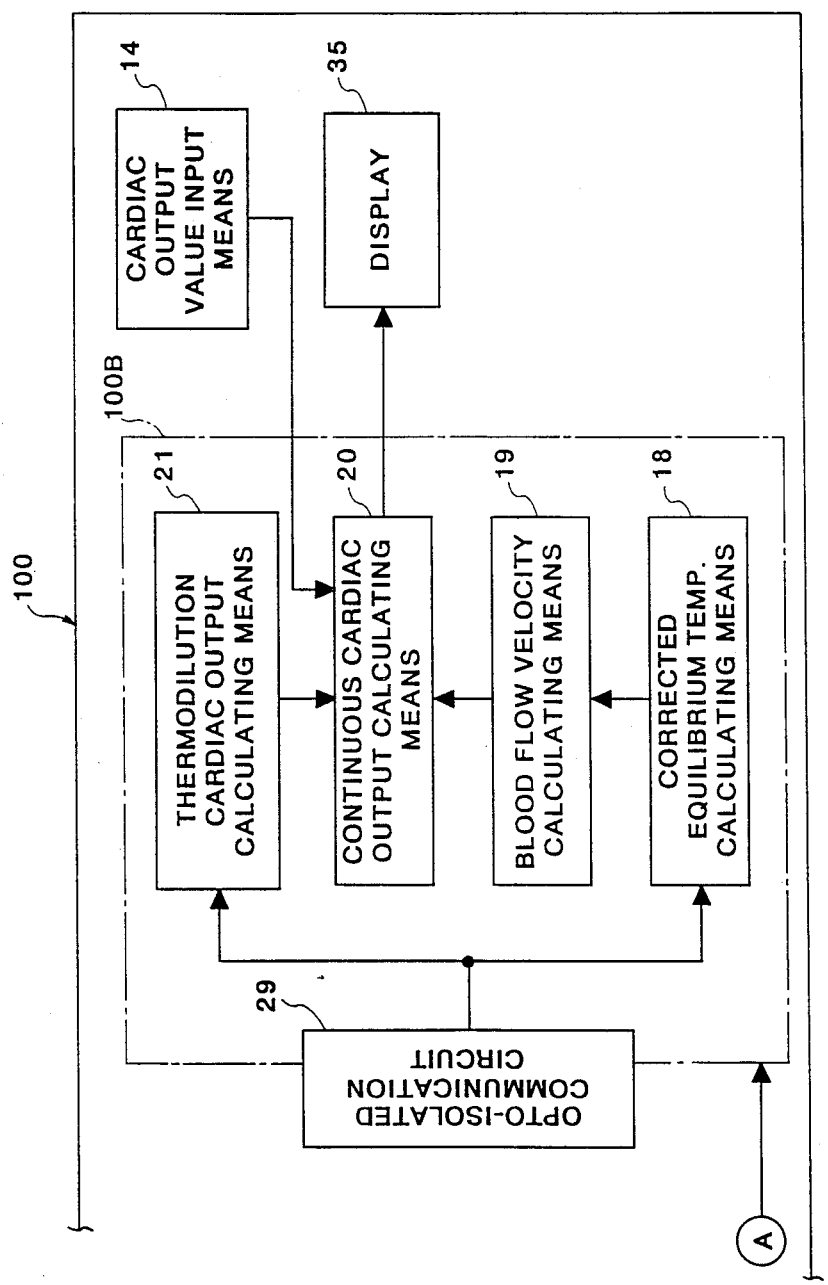

FIG. 1A and 1B are block diagrams illustrating a cardiac output measurement system according to the present invention. As shown in the figure, the system includes a main unit 100, a first catheter 2, and a second catheter 7. The first and second catheters 2 and 7 are provided for the measurement of cardiac output, and they are connected to the main unit 100 through connectors, described later, in such a manner that each of the catheters 2 and 7 can be replaced with different catheters.

Among the two catheters 2 and 7, the first catheter 2 serves as a catheter through which an injectate is injected during the application of a thermodilution method, and which is used to detect the temperature of the injectate. The first catheter 2 accommodates therein a probe circuit for sensing the temperature of the injectate which in turn includes a temperature-sensitive element 3, consisting of, e.g., a thermister, for detecting the temperature of the injectate, and a compensation resistor 4 for compensating for a variation in the characteristic of the temperature-sensitive element 3.

The injectate temperature sensing probe circuit is electrically connected to a measurement section 100A of the main unit 100 through a connector 5 of the first catheter 2 and a connector 6 provided on the main unit 100. During a cardiac output measurement operation, the first catheter 2 is positioned in the right atrium RA of the heart of a patient.

The second catheter 7 serves as a catheter used to detect the temperature of blood and the velocity of the flow thereof. The second catheter 7 accommodates therein two probe circuits, i.e., a blood temperature sensing probe circuit and a temperature-responsive blood flow velocity obtaining probe circuit. The blood temperature sensing probe circuit includes a thermister 8 for sensing the blood temperature thermally diluted in the right atrium RA and the right ventricle RV, and a compensation resistor 9 for compensating for a variation in the characteristic of the thermister 8. The temperature-responsive blood flow velocity obtaining probe circuit includes a thermister 10 (preferably consisting of a self-heating thermister) for obtaining the blood flow velocity by a blood velocity measurement method.

The temperature-responsive blood flow velocity obtaining probe circuit is connected to a resistor 13 serving as an electrical passive element for coping with various degrees of changes in the temperature of the blood flow velocity obtaining thermister 10 which are caused by changes in the temperature of the blood surrounding the thermister 10. In the illustrated example, the resistor 13 serving as the electrical passive element is disposed in a connector 11 of the second catheter 7.

The blood temperature sensing probe circuit and the temperature-responsive blood flow velocity obtaining probe circuit are connected to the measurement section 100A of the main unit 100 through the connector 11 of the second catheter 7 and a connector 12 provided on the main unit 100. During a cardiac output measurement operation, the second catheter 7 is positioned in the pulmonary artery.

The first and second catheters 2 and 7 may be manufactured in such a manner as to give an integrated exterior appearance. They may alternatively have an arrangement in which an injectate injecting mechanism (not shown) of the first catheter 2 alone is integrated with the second catheter 7 while the above-described injectate temperature sensing probe circuit is independently provided and is inserted in an injectate injection tank (not shown).

The main unit 100 basically comprises the following: the measurement section 100A which is connected to the above-described first and second catheters 2 and 7, and is operable to perform the measurement of the resistance of the electrical passive element 13 as well as the measurement of various temperatures; a main CPU section 100B connected to the measurement section 100A through an opto isolation communication circuit 29; a power source section 100C; a cardiac output value input means 14; and a display 35. The arrangement of the measurement section 100A, the main CPU section 100B, and the power source section 100C is such that the sections 100A and 100B are electrically separated from each another so that various data on the measured temperatures will not be influenced by noise or the like. Specifically, the opto-isolation communication circuit 28 between these sections 100A and 100B comprises a first light transmitting and receiving circuit (not shown) formed by a photo-diode circuit and a photo-transistor circuit provided in the measurement section 100A, and a second light transmitting and receiving circuit (not shown, either) formed by a photo-diode circuit and a photo-transistor circuit provided in the main CPU section 100B. The first and second light transmitting and receiving circuits are electrically isolated from each other, with a signal transmission medium, such as an optical fiber glass medium, being interposed between these circuit, so that any electrical noise or the like can be blocked. With this arrangement, absolutely no electrical connection can be established between a voltage signal in the measurement section 100A and a voltage signal in the main CPU section 100B. It is therefore possible to avoid the risk of any closed loop being formed between the human body and the main CPU section 100B. In this way, safe and stable measurement can be performed.

The main CPU section 100B is operable either in a thermodilution mode in which cardiac output values are intermittently obtained by a thermodilution method before they are finally output and displayed, or in a blood flow velocity measurement mode in which cardiac output is continuously calculated by blood velocity measurement and corrected equilibrium temperature calculation, and the result of the calculation is output. The display 35 is connected to the main CPU section 100B in order to allow the calculated and obtained cardiac output values to be finally output and displayed. The cardiac output value input means 14 is connected to the main CPU section 100B in order to input a set cardiac output value.

The power source section 100C supplies direct current to each of the sections 100A and 100B. The section 100C includes a power transformer 30 connected to an external power source and operable to drop the voltage of alternating current from the external source to a predetermined voltage, and a DC power supply 31 to which the resultant AC is supplied. The DC power supply 31 smooths and stabilizes the predetermined-voltage AC output by the power transformer 30 so as to convert the same into a DC voltage. The circuit 31 supplies the resultant DC voltage to a DC/DC converter circuit 32 as well as to the main CPU section 100B via different paths, whereby the DC voltage is independently supplied to the measurement section 100A and the main CPU section 100B for use therein. This arrangement makes it possible to avoid any noise, particularly, in the measurement section 100A and the power source section 100C.

Various blocks of the measurement section 100A will be described. An injectate temperature measurement circuit 25 detects the temperature of an injectate charged from a charge opening (not shown) of the first catheter 2 into the right atrium RA, and it outputs a voltage signal indicative of the detected injectate temperature.

A blood temperature measurement circuit 15 is connected to the blood temperature sensing probe circuit of the second catheter 7 so as to detect the temperature of blood surrounding the catheter 7, and output a voltage signal indicative of the detected blood temperature.

An equilibrium temperature measurement circuit 16 is connected to the temperature-responsive blood flow velocity obtaining probe circuit of the catheter 7, and it is also connected to a constant current device 22. With this arrangement, the circuit 16 detects the equilibrium temperature achieved as a result of the equilibrium between the quantity of heat being generated by the self-heating thermister 10 by utilizing constant current and the quantity of heat being dissipated by the flow of blood surrounding the second catheter 7. The circuit 16 then outputs a voltage signal indicative of the detected equilibrium temperature.

A passive element characteristic value measurement circuit 17 is also connected to the second catheter 7 so as to detect a characteristic value of the electrically passive element 13 connected to the temperature-responsive blood flow velocity obtaining probe circuit, and output a voltage signal indicative of the detected characteristic value. The passive element characteristic value measurement circuit 17 may alternatively be used in an arrangement in which the resistor serving as the electrically passive element 13 provided in the temperature-responsive blood flow velocity obtaining probe circuit is connected, by the switching of an analog switch 26, to either the injectate temperature sensing probe circuit or the blood temperature sensing probe circuit, and in which the passive element characteristic value measurement circuit 17 is used in combination with either the injectate temperature measurement circuit 25 or the blood temperature measurement circuit 15.

The measurement section 100A also has a local CPU 28 serving as a slave computer which operates by following various commands from the main CPU section 100B. In order to execute the commands, the local CPU 28 outputs various control signals to the above-described detection-related circuits. Specifically, the CPU 28 operates to control the measurement actions of the injectate temperature measurement circuit 25, the blood temperature measurement circuit 15, the equilibrium temperature measurement circuit 16, and the passive element characteristic value measurement circuit 17. Furthermore, the local CPU 28 sends a selection signal by which the signal to be input to the analog switches 26 is selected from among various signals, the selected signal being converted by an A/D converter 27 into corresponding digital data, which is fed to the local CPU 28. The local CPU 28 also has an internal arrangement for performing the serial communication function by which various command signals are received from the main CPU section 100B, and the digital data obtained from the detection-related circuits are converted into serial transmission data and are then delivered via the opto-isolation communication circuit 29 to the main CPU section 100B.

Next, various blocks of the main CPU section will be described. The blocks include means to which various functions are allotted so as to execute a program, described later. A thermodilution cardiac output calculating means 21 receives the detected temperature of the injectate as well as the thermally diluted temperature of blood, so as to calculate the thermodilution cardiac output on the basis of these temperatures, and output the result of this calculation to a continuous cardiac output calculating means 20.

When a cardiac output measurement operation is performed with respect to a seriously ill patient and, accordingly, it is impossible to inject an injectate for the adoption of the thermodilution mode, the measurement is performed by adopting the blood flow velocity measurement mode. In this mode, a suitable cardiac output value is input through the cardiac output value input means 14, and the value is input, as the thermodilution cardiac output value, to the continuous cardiac output calculating means 20.

A corrected equilibrium temperature calculating means 18 of the section 100B is continuously supplied with each of the thermal equilibrium temperature of the thermister 10 during heating, the temperature variation compensating constant whose value corresponds to the voltage value based on the characteristic value of the resistor serving as the electrically passive element 13 provided in the temperature-responsive blood flow velocity obtaining probe circuit, and the blood temperature stored and held during the adoption of the thermodilution mode, which is for use in the calibration of cardiac output. On the basis of these input data, the corrected equilibrium temperature calculating means 18 calculates corrected thermal equilibrium temperature of the self-heating thermister 10 in accordance with the following equation (2), then it continuously outputs the result of this calculation.

$$Ttcor = Ttobs - (Tbobs - Tbcal) K \qquad (2)$$

where Ttcor: corrected thermal equilibrium temperature of self-heating thermister, Ttobs: temperature of thermister during heating, Tbobs: blood temperature, Tbcal: blood temperature for use in cardiac output calibration, and K: temperature variation compensating constant The above-stated equation (2) is an example of an usable equation, and is directed to the compensation for variations in the temperature of the blood flow velocity obtaining thermister 10 which are caused by changes in the temperature of blood surrounding the thermister 10. A different equation may be used in so far as it expresses a relationship of the above-described changes in the temperature of blood.

The main CPU section 100B also includes a blood flow velocity calculating means 19 which is continuously supplied with the corrected thermal equilibrium temperature of the self-heating thermister 10 which has been calculated by the corrected equilibrium temperature calculating means 18. The blood flow velocity calculating means 19 calculates, on the basis of the supplied data, the blood flow velocity, then outputs the result of this calculation.

The continuous cardiac output calculating means 20 calculates a parameter concerning the cross-sectional area of the pulmonary artery (the parameter is obtained after having been calibrated concerning changes in the cross-sectional area of the blood vessel). This parameter is calculated on the basis of the thermodilution cardiac output calculated by the thermodilution output calculating means 21 during the adoption of the thermodilution mode and on the basis of the blood flow velocity calculated by the blood flow velocity calculating means 19. The calculated parameter is stored in a register (not shown). Then, the calculating means 20 operates to calculate, on the basis of the blood flow velocity continuously calculated by the blood flow velocity calculating means 19 and on the basis of the blood-vessel cross-sectional area parameter stored in the register, continuous cardiac output, and outputs the result of this calculation.

The display 35 is continuously supplied with the continuous cardiac output calculated by the continuous cardiac output calculating means 20, and finally outputs to display the supplied data.

Figure 2A:
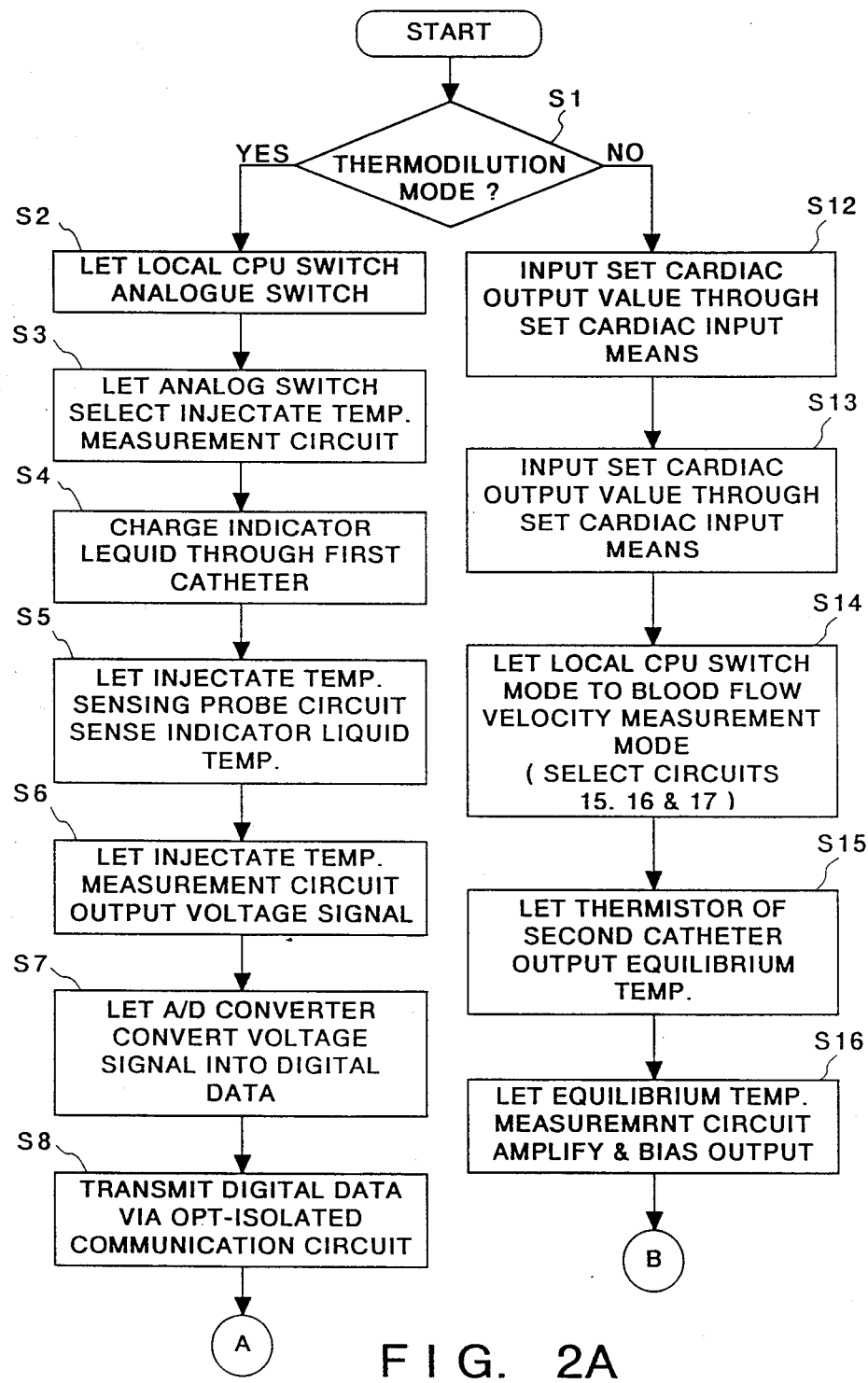
FIGS. 2A, 2B and 3 are flowcharts illustrating examples of control performed by the cardiac output measurement system.
Figure 2B:
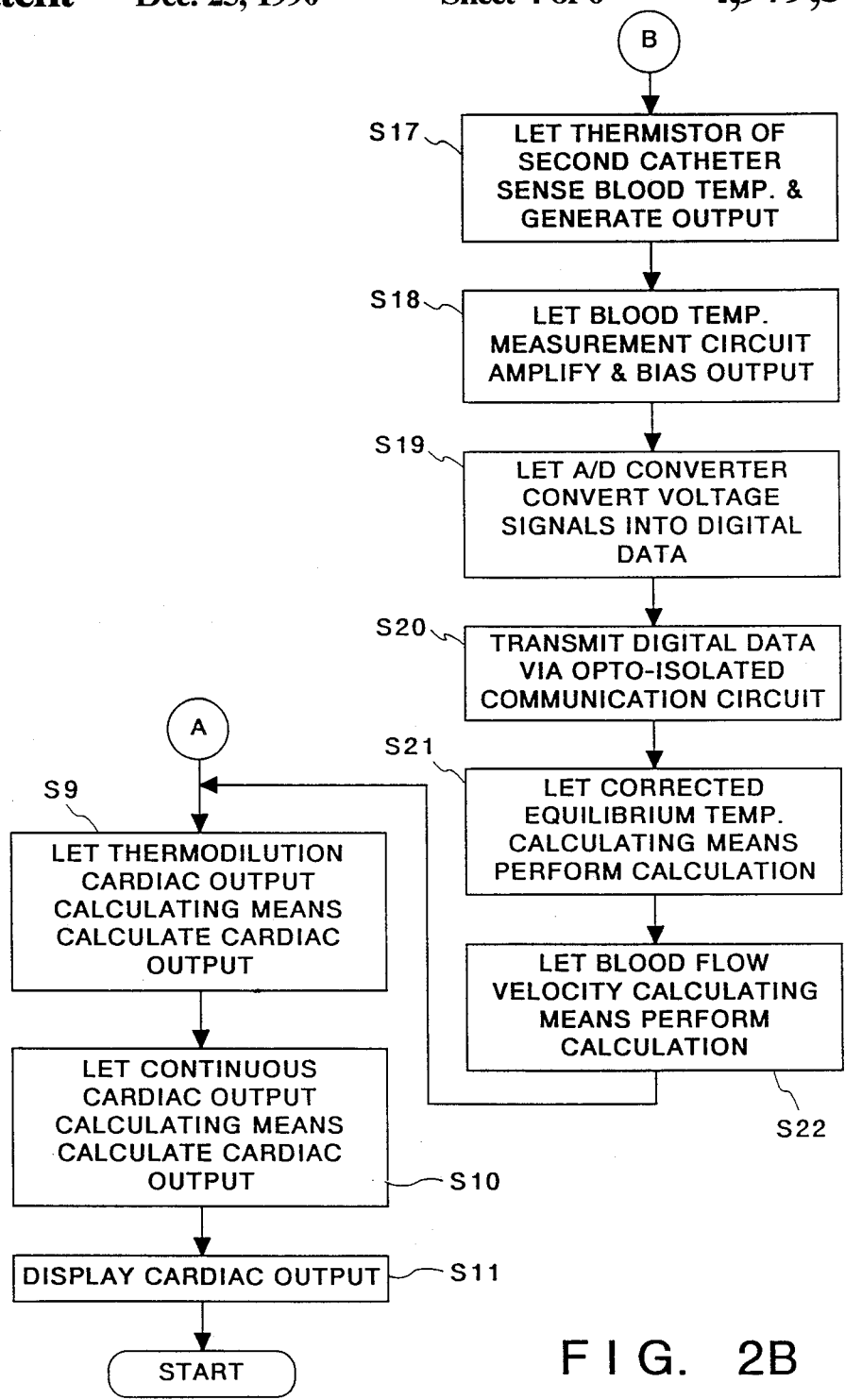
Figure 3:
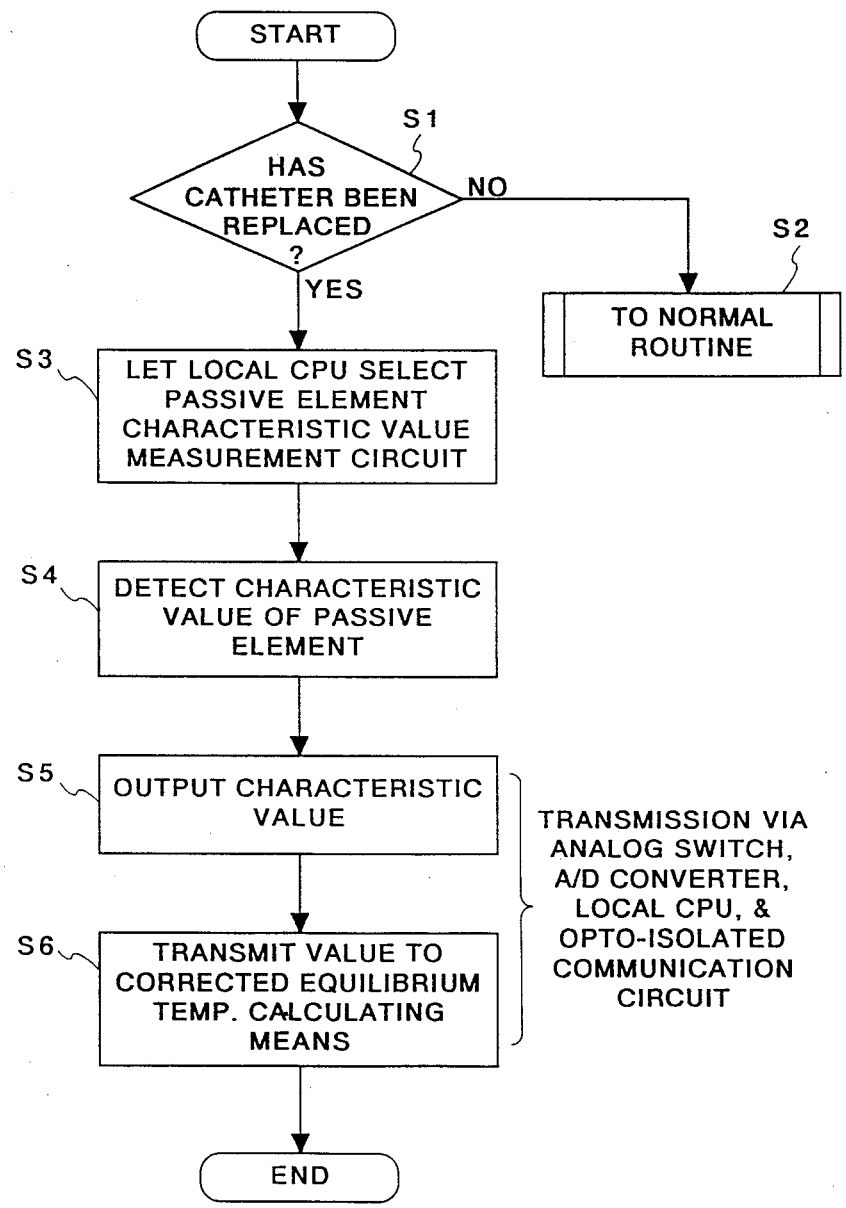
Figure 4:
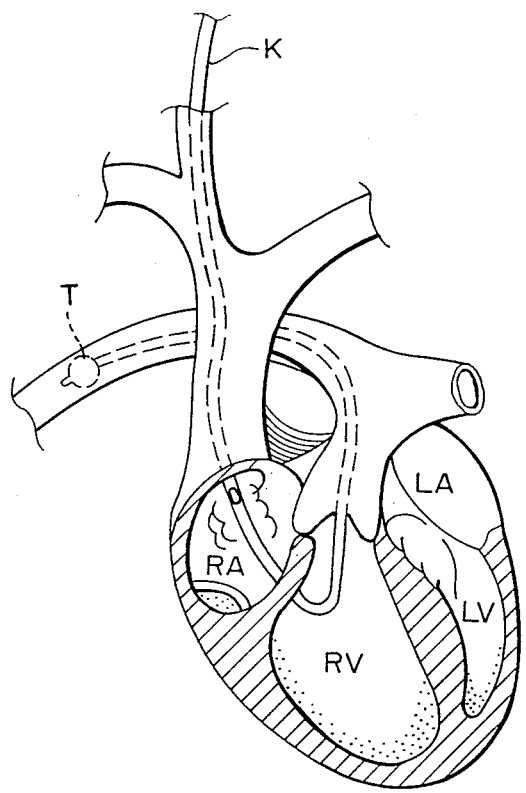
FIG. 4 is a view illustrating the manner in which a catheter is introduced according to the prior art.
Figure 5:
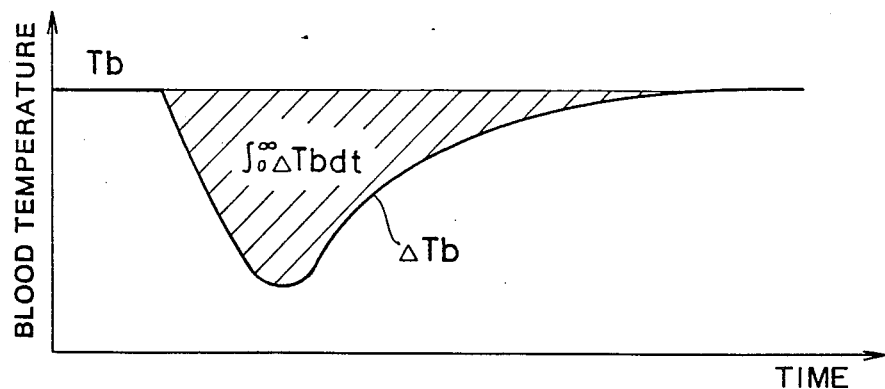
FIG. 5 is a graph showing a thermodilution curve.

The operation of the system will now be described with reference to the flowcharts. FIGS. 2A, 2B and 3 are flowcharts illustrating examples of control performed by the cardiac output measurement system. Referring to FIG. 2A and 2B, when the system is started, a determination is made in Step S1 as to whether the thermodilution mode is adopted. If the adoption of the thermodilution is determined, the program proceeds to Step S2 in which the local CPU 28 outputs a certain switching signal to the analog switch 26, whereby the injectate temperature measurement circuit 25 is selected (Step S3).

Subsequently, in Step S4, an injectate is charged through the first catheter 2. In Step S5, the injectate temperature sensing probe circuit senses the temperature of the injectate injectate. In Step S6, the injectate temperature measurement circuit 25 outputs a voltage signal indicative of the sensed injectate temperature. In the following step S7, the A/D converter 27 converts the voltage signal into a corresponding digital data. In Step S8, the thus obtained digital data is then transmitted via the opto-isolation communication circuit 29 to the thermodilution cardiac output calculating means 21 within the main CPU section 100B. Upon the reception of the data, the calculating means 21 calculates, in Step S9, thermodilution cardiac output by the application of the thermodilution mode.

In the subsequent step S10, the continuous cardiac output calculating means 20 is operated to calculate cardiac output on the basis of the thermodilution cardiac output. The result of this calculation is finally output and displayed by the display 35 in Step S11. Thereafter, the above-described steps are repeated.

On the other hand, if, in Step S1, the adoption of the blood flow velocity measurement mode, not the adoption of the thermodilution mode, has been determined, the program proceeds to Step S12 in which a set cardiac output value is input through the cardiac output value input means 14. In Step S13, the set cardiac output value is input, as the calibration value, to the continuous cardiac output calculating means 20.

In order to execute the blood flow velocity measurement mode, the local CPU 28 selects the blood temperature measurement circuit 15, the equilibrium temperature measurement circuit 16, and the passive element characteristic value measurement circuit 17 (Step S14). Subsequently, in Step S15, the thermister 10 of the second catheter 7 obtains the equilibrium temperature and generates an output, and, in Step S16, this output expressing the obtained equilibrium temperature is amplified and biased by the equilibrium temperature measurement circuit 16.

In Step S17, the thermister 8 of the second catheter 7 senses the blood temperature and generates an output, and, in Step S18, this output expressing the sensed blood temperature is amplified and biased by the blood temperature measurement circuit 15.

The detection signals processed in this way are converted from voltage signals into digital data by A/D converter 27 (Step S19). The digital data resulting from this conversion are, in Step S20, transmitted via the opto-isolation communication circuit 29 to the main CPU section 100B. The corrected equilibrium temperature calculating means 18 calculates corrected equilibrium temperature in accordance with the above-stated equation (2) (Step S21).

In the following step S22, the blood flow velocity calculating means 19 calculates the blood flow velocity. The program then proceeds to Step S10 in which the continuous cardiac output calculating means 20 operates to calculate cardiac output on the basis of the calculated corrected equilibrium temperature and the blood flow velocity. The result of the calculation is finally output and displayed by the display 35 in Step S11. Thereafter, the above-described steps are repeated.

As described above, the blood temperature that is related with the obtained information on the blood flow velocity sensed by the blood flow velocity sensing thermister is corrected by performing a certain calculation on the basis of information on blood temperature. Furthermore, the connector of the probe (catheter) is provided with an electrically passive element such as a resistor, while the means for reading the characteristic value of the passive element is provided in the main unit of the system, so that the characteristic value of the passive element is read by the main unit. With this arrangement, the characteristic of a particular probe (catheter) is automatically determined, and enabling the calculation for correction to be performed in accordance with the characteristic of the relevant probe (catheter). By virtue of the above-described features, according to the present invention, cardiac output can be measured with improved level of precision, without requiring any extra effort by the operator.

The present invention provides the following advantages.

The above-described prior art concerning cardiac output measurement that employs thermodilution or another form of an indicator dilution method performs measurement in an intermittent manner. Consequently, the prior art cannot be used in a continuous measurement operation of the cardiac output. In contrast, the method and the system according to the present invention are capable of overcoming this drawback.

If the measurement of cardiac output is repeated very frequently, this leads to an increase in the total amount of the injectate liquid, thereby involving increased burden upon the patient and increased risk of injection during measurement. The method and the system of the present invention are capable of avoiding this disadvantage.

In a cardiac output measurement system adapted to perform cardiac output measurement continuously, the following problem may arise. The temperature of the blood flow velocity obtaining means of the system fluctuates with changes in the body temperature, i.e., with changes in the blood temperature. This results in the cardiac output values calculated on the basis of the output of the blood flow velocity obtaining means deviating from the correct value, thereby leading to a degradation in the level of measurement precision. The present invention is capable of overcoming this problem.

When a probe possessing a characteristic different from that of a standard probe usually used to perform measurement is used, the following problem may arise. Because of the different characteristic of the used probe, a different body temperature, i.e., a different blood temperature is sensed. This results in a different cardiac output value being calculated, thereby leading to a degradation in the level of measurement precision. The present invention is capable of overcoming this problem.

In brief, the cardiac output measurement method and system according to the present invention are capable of performing cardiac output measurement continuously with reduced burden on the patient and with reduced risk of infection, while being capable of assuring a satisfactory level of measurement precision without requiring any extra effort by the measurer even when the blood temperature changes or when a probe possessing different characteristic is used.

What is claimed is:

1. A cardiac output measurement method which performs a calibration of cardiac output by employing a blood flow velocity measurement method and which performs continuous measurement of cardiac output, comprising the steps of:
   sensing blood temperature;
   generating a blood temperature signal indicative of the sensed blood temperature;
   sensing a cooling temperature of blood flow being heated by a supply of a constant electric current;
   generating an equilibrium temperature signal indicative of the sensed cooling temperature of the blood flow being heated;
   performing a calculation upon the reception of said blood temperature signal and said equilibrium temperature signal in such a manner as to correct a value indicated by said equilibrium temperature signal by a suitable value corresponding to a value indicated by said blood temperature signal, said calculation being followed by generation of a corrected equilibrium temperature signal indicative of the result of said calculation; and
   calculating cardiac output on the basis of a value indicated by said corrected equilibrium temperature signal.

2. A cardiac output measurement method according to claim 1, further comprising the steps of:
   sensing, by means of a passive element, one of said blood temperature and said cooling temperature of blood flow being heated by the supply of constant electric current, said sensing being followed by the generation of a characteristic value signal indicative of characteristic value of said passive element; and
   performing a further calculation for correcting the value indicated by said equilibrium temperature signal on the basis of the characteristic value indicated by said characteristic value signal, said further calculation being followed by the generation of a corrected equilibrium temperature signal.

3. A cardiac output measurement system which performs a calibration of cardiac output by employing a blood flow velocity measurement method and which performs continuous measurement of cardiac output, comprising:
   blood temperature sensing means for sensing blood temperature;
   blood temperature measurement circuit means coupled to said blood temperature sensing means for generating a blood temperature signal indicative of the sensed blood temperature;
   equilibrium temperature obtaining means for sensing a cooling temperature of blood flow being heated by a heating means supplied with a constant electric current; equilibrium temperature measurement circuit means connected to said equilibrium temperature obtaining means so as to generate an equilibrium temperature signal indicative of the sensed cooling temperature of blood flow heated;
   corrected equilibrium temperature calculating means for receiving said blood temperature signal and said equilibrium temperature signal, for performing calculation whereby the value indicated by said equilibrium temperature signal is corrected by a suitable value corresponding to the value indicated by said blood temperature signal, and for generating a corrected equilibrium temperature signal indicative of the result of said calculation; and
   cardiac output calculating means for calculating cardiac output on the basis of a value indicated by said corrected equilibrium temperature signal.

4. A cardiac output measurement system according to claim 3, further comprising:
   characteristic value measurement circuit means including a passive element provided in one of said blood temperature sensing means and said equilibrium temperature obtaining means for generating a characteristic value signal indicative of a characteristic value of said passive element; and
   corrected equilibrium temperature calculating circuit means for performing a calculation for correcting the value indicated by said equilibrium temperature signal on the basis of the characteristic value indicated by said characteristic value signal, and for generating a corrected equilibrium temperature 5. A cardiac output measurement system according to claim 4, wherein said passive element comprises a resistor.

6. A cardiac output measurement system according to claim 3, wherein said blood temperature sensing means, said blood temperature measurement circuit means, said equilibrium temperature obtaining means and said equilibrium temperature measurement circuit means are optically coupled to said corrected equilibrium temperature calculating means and to said cardiac output calculating means, said corrected equilibrium temperature calculating means being electrically coupled to said cardiac output calculating means.

7. A cardiac output measurement system according to claim 3, further comprising means for supplying power to said blood temperature sensing means, to said blood temperature measurement circuit means, to said equilibrium temperature obtaining means and to said equilibrium temperature measurement circuit means via a path different from a path through which power is supplied to said corrected equilibrium temperature calculating means and to said cardiac output calculating means.

* * * * *

UNITED STATES PATENT AND TRADEMARK OFFICE
CERTIFICATE OF CORRECTION

PATENT NO. : 4,979,514
DATED : December 25, 1990
INVENTOR(S) : SEKII et al

It is certified that error appears in the above-identified patent and that said Letters Patent is hereby corrected as shown below:

Title page, Section [56] References Cited, insert under "U.S. PATENT DOCUMENTS":

--3,438,253  11/1966  Kuether et al--

Signed and Sealed this

Tenth Day of November, 1992

Attest:

DOUGLAS B. COMER

*Attesting Officer*    Acting Commissioner of Patents and Trademarks